United States Patent [19]

Rentzea et al.

[11] 4,427,688
[45] Jan. 24, 1984

[54] N-SUBSTITUTED 2-METHYLNAPHTHYLAMIDES, THEIR PREPARATION, AND THEIR USE FOR CONTROLLING FUNGI

[75] Inventors: Costin Rentzea, Heidelberg; Bernd Zeeh; Eberhard Ammermann, both of Ludwigshafen; Gerhard Hamprecht, Weinheim; Ernst-Heinrich Pommer, Limburgerhof, all of Fed. Rep. of Germany

[73] Assignee: BASF Aktiengesellschaft, Fed. Rep. of Germany

[21] Appl. No.: 377,968

[22] Filed: May 13, 1982

[30] Foreign Application Priority Data

May 25, 1981 [DE] Fed. Rep. of Germany ....... 3120804

[51] Int. Cl.³ .................... A61K 31/38; C07D 275/02
[52] U.S. Cl. .................................. 424/270; 424/269; 548/127; 548/128; 548/134; 548/136; 548/194; 548/200; 548/214
[58] Field of Search ............... 548/127, 131, 134, 136, 548/128, 194, 214, 200; 424/270, 269

[56] References Cited

FOREIGN PATENT DOCUMENTS 2625285 12/1976 Fed. Rep. of Germany ...... 548/131

OTHER PUBLICATIONS

R. Wegler, Chemie der Pflanzenschutz-und Schädlingsbekämpfungsmittel, vol. 2, pp. 65, 66 & 109 and vol. 4, pp. 139 & 191, Springer-Verlag, Berlin/Heidelberg/New York (1970).

Primary Examiner—Donald G. Daus
Assistant Examiner—James H. Turnipseed
Attorney, Agent, or Firm—Keil & Witherspoon

[57] ABSTRACT

N-Substituted 2-methylnaphthylamides of the formula

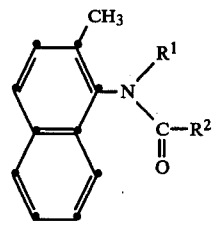

where $R^1$ and $R^2$ have the meanings given in the description, their preparation and their use for controlling fungi.

3 Claims, No Drawings

N-SUBSTITUTED 2-METHYLNAPHTHYLAMIDES, THEIR PREPARATION, AND THEIR USE FOR CONTROLLING FUNGI

The present invention relates to N-substituted 2-methylnaphthylamides, processes for their preparation and fungicides containing these compounds as active ingredients.

The use of zinc ethylene-1,2-bis-dithiocarbamate, N-trichloromethylthiophthalimide and N-trichloromethylthiotetrahydrophthalimide as fungicides in agriculture and horticulture has been disclosed. The said compounds are good agents for combating fungus diseases (R. Wegler, Chemie der Pflanzenschutz-und Schädlingsbekämpfungsmittel, Volume 2, pages 65 to 66 and 109 and Volume 4, pages 139 and 191, Springer-Verlag, Berlin/Heidelberg/New York (1970) and (1977)). However, these fungicides cannot be used once infection has set in, and they are not sufficiently effective in practice when low concentrations are applied.

We have found that N-substituted 2-methylnaphthylamides of the formula

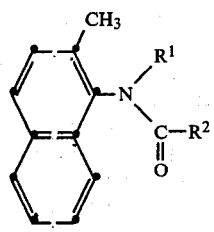 (I)

where $R^1$ is —CH(CH$_3$)—COOCH$_3$,

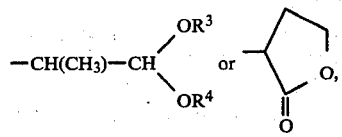

where $R^3$ and $R^4$ independently of one another are methyl or ethyl, or $R^3$ and $R^4$ together are alkylene of 2 or 3 carbon atoms which is unsubstituted or substituted by methyl or ethyl, and $R^2$ is a 5-membered heterocyclic ring which contains a sulfur atom and not more than two nitrogen atoms and is unsubstituted or substituted by methyl or ethyl, have powerful fungicidal properties.

In formula I, $R^2$ is preferably isothiazol-3-, -4- or -5-yl, 3-methylisothiazol-4-yl, 3-methylisothiazol-5-yl, 5-nitroisothiazol-3-yl, thiazol-2-, -4- or -5-yl, 2-bromothiazol-4-yl, 2-bromothiazol-5-yl, 5-nitrothiazol-2-yl, 4-nitrothiazol-2-yl, 4-methylthiazol-5-yl, 2-chloro-4-methylthiazol-5-yl, 1,2,3-thiadiazol-4-yl, 1,2,3-thiadiazol-5-yl, 5-chloro-1,2,4-thiadiazol-4-yl, 1,2,4-thiadiazol-3-yl, 1,2,4-thiadiazol-5-yl, 1,2,5-thiadiazol-3-yl, 1,3,4-thiadiazol-2-yl or 2-chloro-1,3,4-thiadiazol-5-yl.

$R^3$ and $R^4$ in

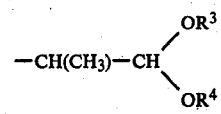

are, for example, methyl or ethyl, or $R^3$ and $R^4$ together are alkylene of 2 or 3 carbon atoms which can be unsubstituted or substituted by methyl or ethyl, so that together with the radical of which $R^3$ and $R^4$ are substituents they form a 1,3-dioxolane or 1,3-dioxane ring which is unsubstituted or substituted by methyl or ethyl.

The N-substituted 2-methylnaphthylamides of the formula I have a chiral carbon atom in $R^1$ and, depending on the nature of $R^1$, other additional chirality centers. The optically pure enantiomers and the diastereomers can be obtained in a conventional manner. Formula I also includes these compounds, in pure form or as mixtures. The pure enantiomers and diastereomers, and the mixtures usually obtained during synthesis, have a fungicidal action.

The compounds of the formula I are obtained by reacting a 2-methylnaphthylamine of the formula

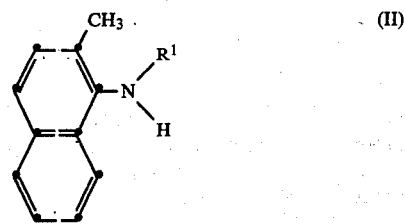 (II)

where $R^1$ has the above meanings,
(a) with an acid halide of the formula

 (III)

where $R^2$ has the above meanings and Hal is chlorine or bromine, or
(b) with an acid anhydride of the formula

 (IV)

where $R^2$ has the above meanings, in the presence or absence of a solvent or diluent, with or without addition of an inorganic or organic base, and with or without addition of an accelerator, at from −10° to +100° C.

Examples of solvents or diluents which are inert towards the reactants are aliphatic or aromatic hydrocarbons, such as pentane, cyclohexane, petroleum ether, benzene, toluene and the xylenes, halohydrocarbons, such as methylene chloride, chloroform, 1,2-dichloroethane and chlorobenzene, ketones, such as acetone and methyl ethyl ketone, ethers, such as diethyl ether, dimethoxyethane, tetrahydrofuran and dioxane, esters, such as ethyl acetate, nitriles, such as acetonitrile, and sulfoxides, such as dimethylsulfoxide, and appropriate mixtures.

Examples of suitable inorganic or organic bases which can be used as acid acceptors in the reaction are alkali metal and alkaline earth metal carbonates, such as sodium or potassium bicarbonate, sodium or potassium carbonate and calcium carbonate, borates, such as sodium borate, phosphates, such as sodium or potassium diphosphate or triphosphate, and amines, such as triethylamine, N,N-dimethylaniline, N,N-dimethylcyclohexylamine, N-methylpiperidine and pyridine. Other conventional bases can also be used. 1 to 10 moles of base are advantageously employed per mole of 2-methylnaphthylamine of the formula II.

The reaction with the acid halide of the formula III can also be carried out without an acid acceptor, and in some cases it is then necessary to pass through dry nitrogen in order to expel the hydrogen halide formed.

Preferred accelerators include metal halides, eg. sodium bromide and potassium iodide, azoles, eg. imidazole and 1,2,4-triazole, pyridines, eg. 4-dimethylaminopyridine, and dimethylformamide. Advantageously, from 0.1 to 1 mole of accelerator is added per mole of 2-methylnaphthylamine of the formula II.

The reactions according to the invention may for example be carried out at from $-10°$ to $+100°$ C., preferably at from $0°$ to $+40°$ C., under atmospheric or superatmospheric pressure, continuously or batchwise.

Compounds of the formula I where $R^1$ is

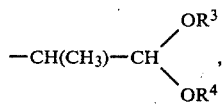

where $R^3$ and $R^4$ together are alkylene of 2 or 3 carbon atoms which is unsubstituted or substituted by methyl or ethyl, and $R^2$ has the above meanings can be obtained by converting a 2-methylnaphthylamide of the formula

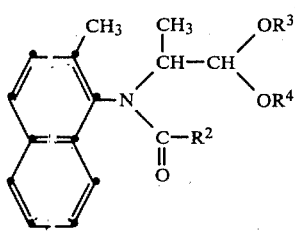

where $R^2$ has the above meanings and $R^3$ and $R^4$ independently of one another are methyl or ethyl, to the corresponding cyclic acetal by splitting off $R^3OH$ and $R^4OH$ to give the corresponding aldehyde and by reaction of the aldehyde with the diol of the formula $HO-R^3-R^4-OH$, where $R^3$ and $R^4$ together are alkylene of 2 or 3 carbon atoms which is unsubstituted or substituted by methyl or ethyl, in the presence or absence of a diluent and with or without addition of an acidic catalyst.

Examples of diols of the formula $HO-R^3-R^4-OH$ are ethylene glycol, propane-1,2-diol, propane-1,3-diol, butane-2,3-diol and neopentylglycol. $R^3OH$ and $R^4OH$ are split off, for example, by the action of a catalytic amount of a strong protic acid or Lewis acid, such as hydrogen chloride, hydrogen bromide, p-toluenesulfonic acid, trifluoroacetic acid, trifluoromethylsulfonic acid, zinc chloride, zinc bromide or boron trifluoride etherate, at from $0°$ C. to the boiling point of the alcohols $R^3OH$ and $R^4OH$. The reaction with a 1,2- or 1,3-diol is carried out, for example, by removing the alcohols $R^3OH$ and $R^4OH$ from the reaction mixture by distillation under reduced or atmospheric pressure or with the aid of an inert gas, such as nitrogen or argon. Suitable solvents or diluents are the above solvents, water or, if used in a stoichiometric amount or in excess, the 1,2- or 1,3-diol itself.

Suitable acidic catalysts are Lewis acids and proton acids, eg. $BF_3$, $AlCl_3$, $ZnCl_2$, mineral acids and sulfonic acids.

Those starting materials of the general formula II which are not already known (from German Laid-Open Application DOS No. 2,845,454 or European Laid-Open Application EP-OS No. 18,510) can be prepared in a conventional manner.

The Examples which follow illustrate the preparation of the novel compounds:

EXAMPLE 1

Preparation of

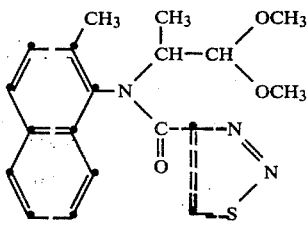

(a) 314 g (2 moles) of 1-amino-2-methylnaphthylamine, 236 g (2 moles) of methylglyoxal dimethyl acetal and 0.4 g of p-toluenesulfonic acid in 1,000 ml of cyclohexane were refluxed for 4 hours, until 36 g of water had been distilled off azeotropically. The cyclohexane was then distilled off under reduced pressure and the residue was further reacted directly. The yield of Schiff base was 493.4 g, corresponding to 96% of theory.

(b) 490 g of the Schiff base were dissolved in 1,500 ml of methanol, and 60 g of sodium borohydride were added at $0°$ C. a little at a time. The mixture was stirred at $20°$ C. for 12 hours, the methanol was distilled off, the residue was dissolved in 1,000 ml of methylene chloride and the solution was stirred with 500 ml of 10% strength potassium hydroxide solution for 30 minutes. The organic phase was then separated off, washed twice with 200 ml of water each time and dried over sodium sulfate. The methylene chloride was distilled off and the residue was distilled under reduced pressure.

367 g (74% of theory) of 2-(N-2'-methyl-1'-naphthyl)-aminopropanol dimethyl acetal of boiling point $140°-145°$ C./0.3 mbar were obtained.

(c) 49.2 g (0.19 mole) of the resulting 2-(N-2'-methyl-1'-naphthyl)-aminopropanol dimethyl acetal were dissolved in 100 ml of dry toluene, and a solution of 28 g (0.19 mole) of 1,2,3-thiadiazole-4-carbonyl chloride (J. Chem. Soc. (1965), 5166) in 30 ml of toluene and a solution of 20 g (0.2 mole) of triethylamine in 30 ml of toluene were added dropwise at the same time (from two dropping funnels) at $25°$ C., while stirring. The mixture was stirred at $25°$ C. for two hours, the precipitate was filtered off with suction and the filtrate was washed three times with 100 ml of water each time, dried over sodium sulfate, decolorized with animal charcoal and concentrated under reduced pressure. The resinous residue was stirred thoroughly four times with 100 ml of warm ($45°$ C.) petroleum ether each time, the petroleum ether was decanted off and the resin was dried at $70°$ C./0.3 mbar for 4 hours. 2-[N-(2-Methyl-1- naphthyl)-N-(1,2,3-thiadiazol-4-yl-carbonyl)]-aminopropanol dimethyl acetal was obtained as a yellowish resin in a yield of 39 g (55.3% of theory).

IR spectrum (film): 3100, 3045, 2980, 2945, 2830, 1640, 1472, 1360, 1310, 1230, 1100, 1060, 960, 810, 780 and 746 cm⁻¹.

EXAMPLE 2

Preparation of

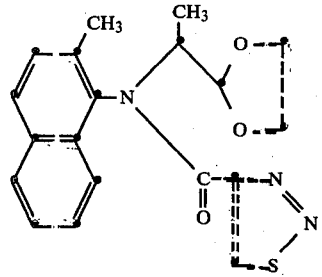

25.7 g (0.069 mole) of the compound prepared in Example 1, 4.9 g of ethylene glycol and 0.2 g of p-toluenesulfonic acid in 150 ml of dry toluene were stirred at 80° C. for 8 hours, during which the methanol formed was continuously expelled from the reaction mixture with a weak stream of nitrogen. The organic solution was cooled, washed three times with 100 ml of water each time and concentrated under reduced pressure, finally at 80° C. and under 0.5 mbar.

19.3 g (75.8% of theory) of 1,2,3,-thiadiazole-4-carboxylic acid N-[1-(1,3-dioxolan-2-yl)-2-methyl-ethyl]-N-2'-methyl-1'-naphthylamide were obtained as a resin.

IR spectrum (film): 3100, 3050, 2980, 2950, 2880, 1640, 1470, 1345, 1230, 1115, 1066, 1025, 940, 810, 782 and 746 cm⁻¹.

EXAMPLE 3

Preparation of

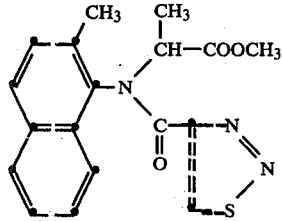

14 g (0.095 mole) of 1,2,3-thiadiazole-4-carbonyl chloride in 30 ml of toluene were added dropwise to a solution of 22.9 g (0.0945 mole) of N-(2-methyl-1-naphthyl)-alanine methyl ester in 100 ml of dry toluene at from +15° C. to +30° C. The mixture was stirred at 80° C. for 8 hours, during which the hydrogen chloride formed was continuously expelled in a weak stream of nitrogen. The mixture was cooled and stirred with a solution of 5 g of sodium bicarbonate in 100 ml of water. The organic phase was separated off, dried over sodium sulfate, decolorized with charcoal and evaporated under reduced pressure. The oily residue which remained was dried at 50° C. and under 0.1 mbar for 3 hours to give 32 g (95.2% of theory) of N-(1,2,3-thiadiazol-4-yl-carbonyl)-N-(2-methyl-1-naphthyl)-alanine methyl ester as a light-brown resin.

IR-spectrum (KBr): 3110, 3060, 3000, 2990, 2955, 1726, 1645, 1496, 1404, 1320, 1282, 1250, 1240, 1128, 1105, 1075, 967, 870, 822, 788, 760 cm⁻¹.

The following compounds for instance were prepared analogously:

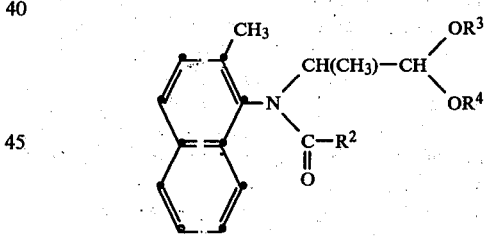

| No. | R² | Physical data |
|---|---|---|
| 4 | 1,2-Thiazol-4-yl | oil |
| 5 | 5-Nitro-1,2-thiazol-3-yl | oil |
| 6 | 1,2-Thiazol-5-yl | |
| 7 | 3-Methyl-1,2-thiazol-4-yl | oil |
| 8 | 1,3-Thiazol-2-yl | m.p. 86–88° C. |
| 9 | 5-Nitro-1,3-thiazol-2-yl | oil |
| 10 | 1,3-Thiazol-4-yl | m.p. 118–120° C. |
| 11 | 2-Bromo-1,3-thiazol-4-yl | oil |
| 12 | 1,3-Thiazol-5-yl | |
| 13 | 5-Methyl-1,3-thiazol-4-yl | m.p. 112–115° C. |
| 14 | 2-Chloro-4-methyl-1,3-thiazol-5-yl | oil |
| 15 | 1,2,3-Thiadiazol-5-yl | m.p. 136–139° C. |
| 16 | 1,3,4-Thiadiazol-2-yl | oil |
| 17 | 1,2,5-Thiadiazol-3-yl | resin |

| No. | R² | R³ | R⁴ | Physical data |
|---|---|---|---|---|
| 18 | 1,2-Thiazol-3-yl | CH₃ | CH₃ | oil |
| 19 | 1,2-Thiazol-4-yl | CH₃ | CH₃ | oil |
| 20 | 1,3-Thiazol-4-yl | CH₃ | CH₃ | oil |
| 21 | 1,3-Thiazol-2-yl | —CH₂—CH₂— | | oil |
| 22 | 5-Nitro-1,3-thiazol-2-yl | CH₃ | CH₃ | oil |
| 23 | 1,3-Thiazol-4-yl | CH₃ | CH₃ | oil |
| 24 | 1,3-Thiazol-5-yl | CH₃ | CH₃ | oil |
| 25 | 1,3-Thiazol-5-yl | —CH₂—CH₂— | | resin |
| 26 | 5-Methyl-1,3-thiazol-4-yl | CH₃ | CH₃ | |
| 27 | 1,2,3-Thiadiazol-4-yl | CH₃ | CH₃ | resin |
| 28 | 1,2,3-Thiadiazol-4-yl | —CH₂—CH₂— | | oil |
| 29 | 1,2,3-Thiadiazol-5-yl | CH₃ | CH₃ | oil |
| 30 | 1,2,5-Thiadiazol-3-yl | CH₃ | CH₃ | resin |
| 31 | 1,2,5-Thiadiazol-3-yl | —CH₂—CH₂— | | resin |

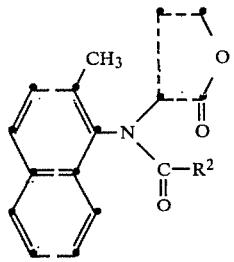

| No. | R² | Physical data |
|---|---|---|
| 32 | 1,2-Thiazol-3-yl | oil |
| 33 | 1,2-Thiazol-4-yl | |
| 34 | 5-Nitro-1,2-thiazol-3-yl | resin |
| 35 | 1,2-Thiazol-5-yl | resin |
| 36 | 3-Methyl-1,2-thiazol-4-yl | oil |
| 37 | 1,3-Thiazol-2-yl | oil |
| 38 | 5-Nitro-1,3-thiazol-2-yl | |
| 39 | 1,3-Thiazol-4-yl | resin |
| 40 | 1,3-Thiazol-5-yl | |
| 41 | 5-Methyl-thiazol-4-yl | resin |
| 42 | 4-Methyl-2-chlorothiazol-5-yl | oil |
| 44 | 1,2,3-Thiadiazol-4-yl | m.p. 180–184° C. |
| 45 | 1,2,3-Thiadiazol-5-yl | resin |
| 46 | 1,2,5-Thiadiazol-4-yl | m.p. 156–169° C. |

The N-substituted 2-methylnaphthylamides of the formula I have a fungitoxic action on phytopathogenic fungi, especially from the Phycomycetes class. The compounds are therefore suitable for instance for combating Phytophthora infestans in tomatoes and potatoes, Phytophthora parasitica in strawberries, Phytophthora cactorum in apples, Pseudoperonospora cubensis in cucumbers, Pseudoperonospora humuli in hops, Peronosphora sparsa in roses, Peronosphora tabacina in tobacco, Plasmopara viticola in grapes, Plasmopara halstedii in sunflowers, Sclerospora macrospora in Indian corn, Bremia lactucae in lettuce, Mucor mucedo in fruit, Rhizopus nigricans in beets, Erysiphe graminis in cereals, Uncinula necator in grapes, Podosphaera leucotricha in apples, Sphaerotheca fuliginea in roses, and Erysiphe cichoriacearum in cucumbers.

The application rates depend on the effect desired, and range from 0.1 to 5 kg of active ingredient per hectare. Some of the active ingredients have curative properties, i.e., the agents may be applied after the plants have been infected by the pathogen, and success is still ensured.

Many of the novel compounds also have a systemic action, which means that visible plant parts can also be protected by a root treatment.

The novel active ingredients are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible. These formulations contain from 0.1 to 95, and preferably from 0.5 to 90, wt.% of active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfonate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wool meal, and nutshell meal, cellulosic powders, etc.

Examples of formulations are given below.

I. 90 parts by weight of compound 3 is mixed with 10 parts by weight of N-methyl-alpha-pyrrolidone. A mixture is obtained which is suitable for application in the form of very fine drops.

II. 20 parts by weight of compound 10 is dissolved in a mixture consisting of 80 parts by weight of xylene, 10 parts by weight of the adduct of 8 to 10 moles of ethylene oxide and 1 mole of oleic acid-N-monoethanolamine, 5 parts by weight of the calcium salt of dodecylbenzenesulfonic acid, and 5 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

III. 20 parts by weight of compound 15 is dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion is obtained containing 0.02% by weight of the active ingredient.

IV. 20 parts by weight of compound 17 is dissolved in a mixture consisting of 25 parts by weight of cyclohexanol, 65 parts by weight of a mineral oil fraction having a boiling point between 210° C. and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 20 parts by weight of compound 30 is well mixed with 3 parts by weight of the sodium salt of diisobutyl-naphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound 44 is intimately mixed with 97 parts by weight of particulate kaolin. A dust is obtained containing 3% by weight of the active ingredient.

VII. 30 parts by weight of compound 46 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 13 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

IX. 20 parts of compound 15 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The agents according to the invention may also be mixed and applied with other active ingredients, e.g., herbicides, insecticides, growth regulators, bactericides, fungicides and fertilizers. When mixed with other fungicides, the spectrum of fungicidal action is in many cases increased; with a number of these fungicidal compositions, synergistic effects also occur; i.e., the fungicidal action of the combination product is greater than the effect of the individual components added together. The spectrum of action is particularly favorably influenced when the compounds according to the invention are mixed with the following fungicides:

manganese N,N-ethylene-bis-dithiocarbamate, manganese zinc N,N-ethylenediamine-bis-dithiocarbamate, the ammonia complex of zinc N,N-ethylene-bis-dithiocarbamate and N,N'-polyethylene-bis-(thiocarbamoyl)-disulfide, N-trichloromethylthiotetrahydrophthalimide, N-trichloromethylthio-phthalimide, 5-ethoxy-3-trichloromethyl-1,2,3-thiadiazole, 2-methoxycarbonylaminobenzimidazole, 2-thiocyanomethylthiobenzothiazole, 1,4-dichloro-2,5-dimethoxybenzene, 2,3-dichloro-6-methyl-1,4-oxathiin-5-carboxylic acid anilide, 2-methyl-5,6-dihydro-4H-pyran-3-carboxylic acid anilide, 2,4,5-trimethylfuran-3-carboxylic acid anilide, 2-methylfuran-3carboxylic acid anilide, 2,5-dimethylfuran-3-carboxylic acid cyclohexylamide, N-cyclohexyl-N-methoxy-2,5-dimethylfuran-3-carboxylic acid amide, 5-methyl-5-vinyl-3-(3,5-dichlorophenyl)-2,4-dioxo-1,3-oxazolidine, and 3-(3,5-dichlorophenyl)-5-methyl-5-methoxymethyl)-1,3-oxazolidine-2,4-dione.

The following list of fungicidal active ingredients with which the compounds according to the invention may be combined is intended to illustrate and not to restrict the combination possibilities. Examples are as follows:

dithiocarbamates and their derivatives, e.g. iron(III) dimethyldithiocarbamate, zinc dimethyldithiocarbamate, zinc N,N-ethylene-bis-dithiocarbamate, tetramethylthiuram disulfide, zinc N,N-propylene-bis-dithiocarbamate, and the ammonia complex of zinc N,N-propylene-bis-dithiocarbamate and N,N'-polypropylene-bis-(thiocarbamoyl)-disulfide, nitrophenol derivatives, e.g. dinitro-(1-methylheptyl)-phenyl crotonate, 2-sec.-butyl-4,6-dinitrophenyl 3,3-dimethylacrylate and 2-sec.-butyl-4,6-dinitrophenyl isopropyl carbonate; heterocyclic compounds, e.g. 2-heptadecyl-2-imidazoline acetate, 2,4-dichloro-6-(o-chloroanilino)-s-triazine, O,O-diethyl phthalimidophosphonothioate, 5-amino-1-(bis-(dimethylamino)-phosphinyl)-3-phenyl-1,2,4-triazole, 2,3-dicyano-1,4-dithioanthraquinone, 2-thio-1,3-dithio-(4,5-b)-quinoxaline, methyl 1-(butylcarbamoyl)-2-benzimidazole-carbamate, 4-(2-chlorophenylhydrazono)-3-methyl-5-isoxazolone, pyridine-2-thio-1-oxide, 8-hydroxyquinoline and its copper salts, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methylpyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, alpha-(2-chloro-phenyl-alpha-(4-chlorophenyl)-5-pyrimidine-methanol, and 1-(4-chlorophenoxy)-3,3-dimethyl-1-(1H-1,2,4-triazol-1yl)-2-butanone.

For the biological experiments, the following compounds were used for comparison purposes:
N-trichloromethylthiophthalimide (A)
N-trichloromethylthiotetrahydrophthalimide (B)
zinc-ethylene-1,2-bis-dithiocarbamate (C).

EXPERIMENT 1

Fungicidal action on emergence diseases in peas 100 g samples of pea seeds of the "Senator" variety were carefully shaken for about 5 minutes in glass bottles with 300 mg (=0.3 wt%) of seed disinfectant formulations containing (dry basis) of 40% of active ingredient. Subsequently, 100 seeds were sown 3 cm deep and 3 to 5 cm apart in pots in a compost naturally and heavily infested with the fungi Pythium spec., Aphanomyces spec. and Fusarium oxysporum. The boxes were set up in the greenhouse at from 17° to 20° C. The number of healthy pea plants was determined after 21 days.

In this test, active ingredients nos. 3, 10, 17, 44 and 46 had a better action than comparative compound B.

EXPERIMENT 2

Action on cucumber mildew

Leaves of pot-grown cucumber seedlings of the "Chinesische Schlange" variety were sprayed at the 2-leaf stage with a spore suspension of cucumber mildew (Erysiphe cichoracearum). After the spray layer had dried overnight, the plants were sprayed with aqueous emulsions consisting of 80% active ingredient and 20% emulsifier. After this sprayed-on layer had dried, the plants were set up in the greenhouse at from 20° to 22° C. and a relative humidity of 70 to 80%. To assess the action of the novel active ingredients, the extent of fungus spread was determined after 8 days.

In this test, active ingredients nos. 1, 3, 15, 17 and 30 had a very good action.

EXPERIMENT 3

Action on Phytophthora infestans in tomatoes

Leaves of potted tomatoes of the "Grobe Fleischtomate" variety were sprayed with aqueous suspensions containing 0.025 wt% of active ingredient. After the sprayed-on layer had dried, the leaves were infected with a zoospore suspension of Phytophthora infestans. The plants were then placed for 5 days in a steam-saturated chamber kept at 16° to 18° C. After this period, the disease had spread on the untreated control plants to such an extent that the fungicidal action of the compounds was able to be assessed.

In this test, active ingredients nos. 1, 2, 3, 8, 10, 12, 44 and 46 had a better action than comparative agent C.

EXPERIMENT 4

Fungicidal action on Plasmopara viticola in grapes

Leaves of potted vines of the Müller-Thurgau variety were sprayed with aqueous suspensions containing 0.025% (wt%) of active ingredient. To assess the duration of action, the plants were set up, after the sprayed-on layer had dried, for 10 days in the greenhouse. Then the leaves were infected with a zoospore suspensions of Plasmopara viticola. The plants were first placed for 16 hours in a steam-saturated (moist) chamber at 24° C., and then in a greenhouse for 8 days at from 20° to 30° C. To accelerate and intensify and sporangiophore discharge, the plants were then again placed in the moist chamber for 16 hours. The extent of fungus attack was then assessed on the undersides of the leaves.

In this test, active ingredients nos. 1, 2, 3, 10, 13, 17, 30, 4 and 46 had a better action than comparative agent A.

We claim:

1. An N-substituted 2-methylnaphthylamide of the formula

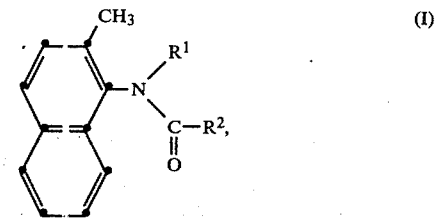

where $R^1$ is —CH(CH$_3$)—COOCH$_3$,

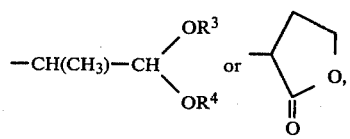

where $R^3$ and $R^4$ independently of one another are methyl or ethyl, or $R^3$ and $R^4$ together are alkylene of 2 or 3 carbon atoms which is unsubstituted or substituted by methyl or ethyl, and $R^2$ is a 5-membered heterocyclic ring in which the ring atoms consist of one sulfur atom and one or two nitrogen atoms and is unsubstituted or mono-substituted by methyl, ethyl, bromine, chlorine nitro or di-substituted by one methyl group and one chlorine atom.

2. A process for combating fungi, wherein the fungi or the objects to be protected against fungus attack are treated with a fungicidally effective amount of an N-substituted 2-methylnaphthylamide of the formula

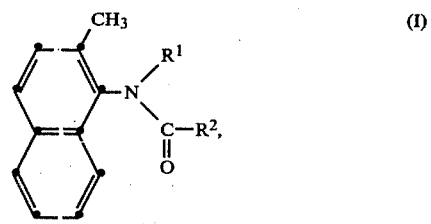

where $R^1$ is —CH(CH$_3$)—COOCH$_3$,

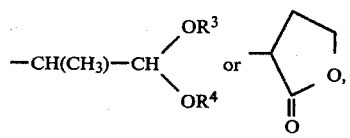

where $R^3$ and $R^4$ independently of one another are methyl or ethyl, or $R^3$ and $R^4$ together are alkylene of 2 or 3 carbon atoms which is unsubstituted or substituted by methyl or ethyl, and $R^2$ is a 5-membered heterocyclic ring in which the ring atoms consist of one sulfur atom and one or two nitrogen atoms and is unsubstituted or mono-substituted by methyl, ethyl, bromine, chlorine or nitro or disubstituted by one methyl group and one chlorine atom.

3. N-substituted 2-methylnaphthylamides of the formula I of claim 1, in which $R^2$ is isothiazol-3-, -4- or -5-yl, 3-methylisothiazol-4-yl, 3-methylisothiazol-5-yl, 5-nitroisothiazol-3-yl, thiazol-2-, -4- or -5-yl, 2-bromothiazol-4-yl, 2-bromothiazol-5-yl, 5-nitrothiazol-2-yl, 4nitrothiazol-2-yl, 4-methylthiazol-5-yl, 2-chloro-4-methylthiazol-5-yl, 1,2,3-thiadiazol-4-yl, 1,2,3-thiadiazol-5-yl, 5-chloro-1,2,4-thiadiazol-4-yl, 1,2,4-thiadiazol-3-yl, 1,2,4-thiadiazol-5-yl, 1,2,5-thiadiazol-3-yl, 1,3,4-thiadiazol-2-yl or 2-chloro-1,3,4-thiadiazol-5-yl.

* * * * *